(12) United States Patent
Zuluaga (10) Patent No.: US 6,904,199 B2
(45) Date of Patent: Jun. 7, 2005

(54) OPTICAL CATHETER WITH DOUBLE-CLAD FIBER

(75) Inventor: Andres Zuluaga, Boston, MA (US)

(73) Assignee: InfraReDx, Inc., Cambridge, MA (US)

( * ) Notice: Subject to any disclaimer, the term of this patent is extended or adjusted under 35 U.S.C. 154(b) by 167 days.

(21) Appl. No.: 10/218,939

(22) Filed: Aug. 14, 2002

(65) Prior Publication Data

US 2004/0034290 A1 Feb. 19, 2004

(51) Int. Cl.[7] .................................................. G02B 6/26

(52) U.S. Cl. ........................................... 385/33; 385/36

(58) Field of Search ............................... 385/33, 31, 36; 606/15, 17, 18; 600/342; 607/92, 93

(56) References Cited

U.S. PATENT DOCUMENTS

| 4,397,524 | A | * | 8/1983 | Yoshimura et al. | .......... 385/116 |
| 4,593,973 | A | * | 6/1986 | Yoshida et al. | ............. 385/126 |
| 4,784,144 | A | * | 11/1988 | Ono et al. | .................. 600/325 |
| 4,896,941 | A | * | 1/1990 | Hayashi et al. | ............. 385/116 |
| 5,625,459 | A | * | 4/1997 | Driver | ........................ 356/446 |
| 6,542,665 | B2 | * | 4/2003 | Reed et al. | .................... 385/34 |
| 6,654,630 | B2 | * | 11/2003 | Zuluaga et al. | ............. 600/476 |
| 6,757,467 | B1 | * | 6/2004 | Rogers | ........................ 385/126 |

* cited by examiner

Primary Examiner—Rodney Bovernick
Assistant Examiner—Mike Stahl
(74) Attorney, Agent, or Firm—Fish & Richardson P.C.

(57) ABSTRACT

A double-clad fiber extends along an axis of a catheter. The fiber has a core and an annular cladding surrounding the core. A lens assembly has a first sub-aperture in optical communication with the core and a second sub-aperture in optical communication with the annular cladding.

27 Claims, 8 Drawing Sheets

OPTICAL CATHETER WITH DOUBLE-CLAD FIBER

FIELD OF INVENTION

This invention relates to catheters, and in particular, to optical catheters.

BACKGROUND

Vulnerable plaques are lipid filled cavities that form within the wall of an artery.

These plaques, when ruptured, can cause massive clotting in the artery. The resultant clot can interfere with blood flow to the brain, resulting in a stroke, or with blood flow to the coronary arteries, resulting in a heart attack.

To locate vulnerable plaques, one inserts a catheter through the lumen of the artery. The catheter includes a delivery fiber for illuminating a spot on the arterial wall and a collection fiber for collecting scattered light that results from that illumination. The delivery fiber and the collection fiber form distinct optical channels within the catheter. The catheter used for locating plaques is thus a multi-channel catheter.

Light scattered as a result of illumination by the delivery fiber is scattered in many directions, both by structures within the wall of the artery and by particles in the blood. This results in a diffuse glow similar to that one experiences in a dense fog. A very small portion of this scattered light ultimately falls on the face of the collection fiber. The remainder of the scattered light, which may contain useful diagnostic information, is simply wasted. Based upon this miniscule fraction of the total available scattered light, a processor determines whether or not the patient's life is endangered by a vulnerable plaque lurking within the arterial wall.

SUMMARY

The invention is based on the recognition that one can recover significantly more light scattered from a particular depth behind an arterial wall by collecting light entering an annular field of view surrounding an illuminated spot on that wall.

In one aspect, the invention features a catheter in which a double-clad fiber extends along an axis thereof. The double-clad fiber has a core and an annular cladding surrounding the core. This double-clad fiber is in optical communication with a lens assembly having at least two sub-apertures. The first sub-aperture is in optical communication with the core; and the second sub-aperture is in optical communication with the annular cladding.

In another aspect, the invention includes a distal tip assembly having a lens assembly for optically coupling to a multi-channel fiber. Such a lens assembly includes first and second sub-apertures for optically coupling to first and second channels of the multi-channel fiber.

Another aspect of the invention is a method for coupling light into and out of an optical catheter. The method includes providing a multi-channel optical fiber that has at least a first and second channel extending along the catheter. A delivery beam is directed along the first channel while light incident on the optical catheter is directed into the second channel.

The invention optionally includes a beam re-director in optical communication with the lens assembly. Examples of beam re-directors include mirrors, a prisms, and other light bending structures.

In some embodiments, the lens assembly is an annular wedge prism. Such a prism can include walls forming a hole defining a first sub-aperture. Alternatively, the first sub-aperture can be central zone having planar proximal and distal faces. The second sub-aperture can include a frusto-conical face.

Other embodiments of the invention include those in which the lens assembly is configured to cause a first beam entering the first sub-aperture and a second beam entering the second sub-aperture to diverge from each other. One lens assembly that can perform this function includes a GRIN ("graduated index of refraction") lens. An example of a GRIN lens suitable for this application is one having a central sub-aperture that is index-matched to the core of the double-clad fiber. Additionally, the GRIN lens may have an annular sub-aperture having a radially varying index of refraction.

The annular wedge prism can be spaced apart from the distal face of the double-clad fiber, or in physical contact with the fiber. In some embodiments, the annular wedge prism is integral with the double-clad fiber. For example, the distal face of the double-clad fiber may itself be shaped to form a portion of the lens assembly.

In some embodiments, the beam re-director performs some of the functions of the annular wedge prism. For example, the beam-redirector may have a central sub-aperture oriented to re-direct a beam in a first direction and an annular sub-aperture oriented to re-direct a beam in a second direction different from the first direction.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

Other features and advantages of the invention will be apparent from the following detailed description, and from the claims.

DETAILED DESCRIPTION

System Overview

Figure 1:
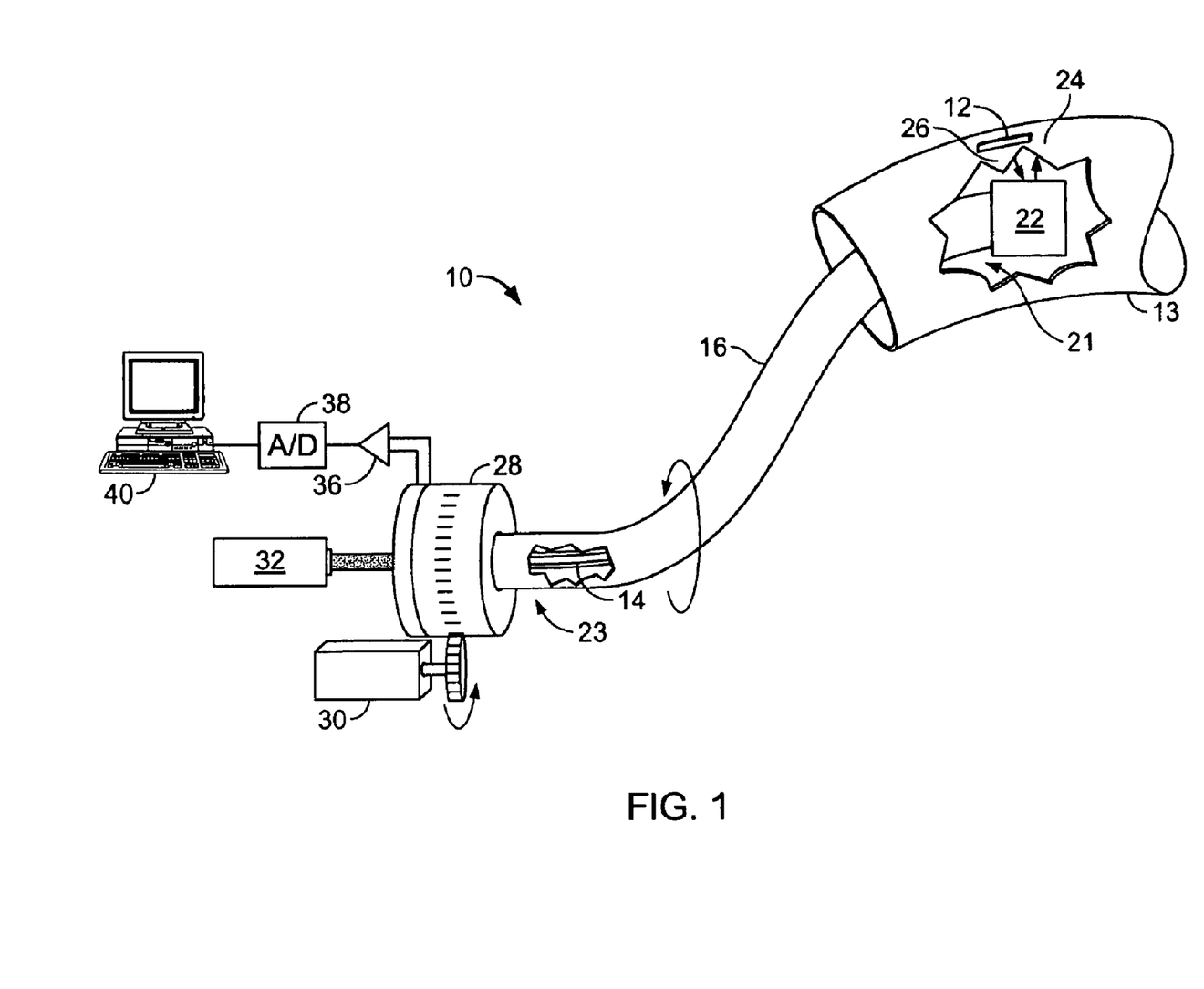
FIG. 1 is a schematic of a system for identifying vulnerable plaque in a patient.

FIG. 1 shows a diagnostic system 10 for identifying vulnerable plaque 12 in an arterial wall 13 of a patient. The diagnostic system features a catheter 16 to be inserted into a selected artery, e.g. a coronary artery, of the patient. A double-clad fiber 14 extends between a distal end 21 and a proximal end 23 of the catheter 16. The double-clad fiber, shown in FIG. 3A, has an outer cladding layer 15, an inner cladding layer 20, and a fiber core 18. In a double-clad fiber 14, light can travel through either the inner cladding layer 20, the fiber core 18, or both.

Figure 2:
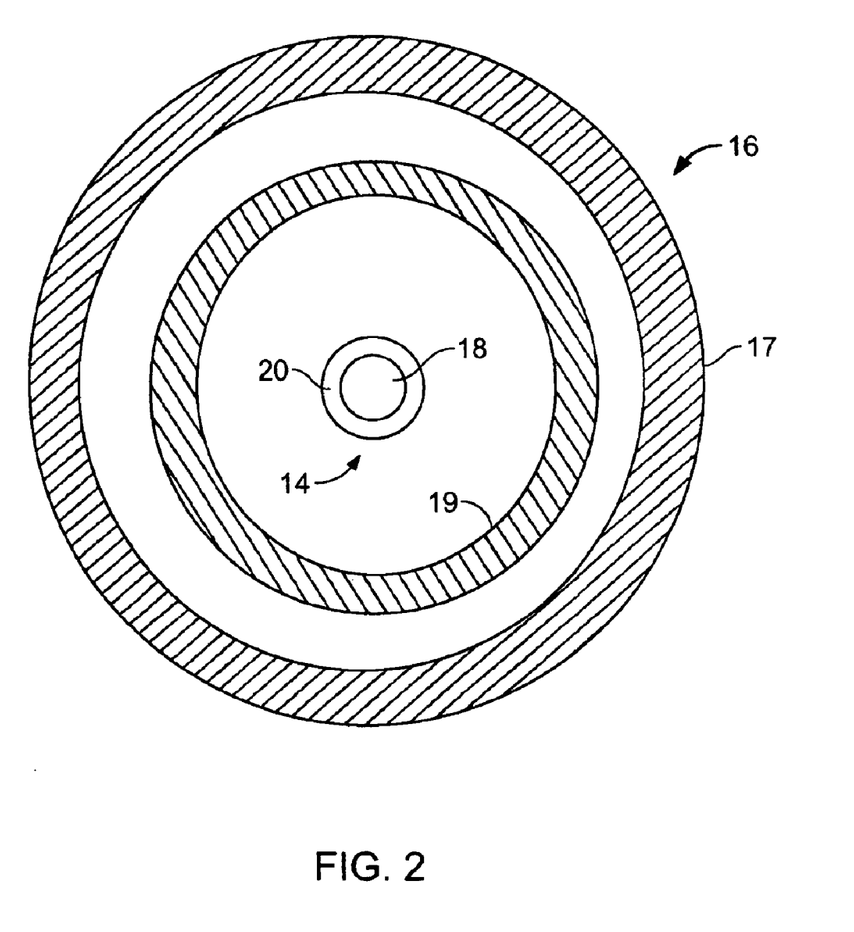
FIG. 2 is a cross-section of the catheter in FIG. 1.

As shown in FIG. 2, the catheter 16 includes a jacket 17 surrounding a rotatable core 19 through the center of which the double-clad fiber 14 extends. The rotatable core 19 spins at rate between approximately 4 revolutions per minute and 30 revolutions per minute.

Figure 3A:
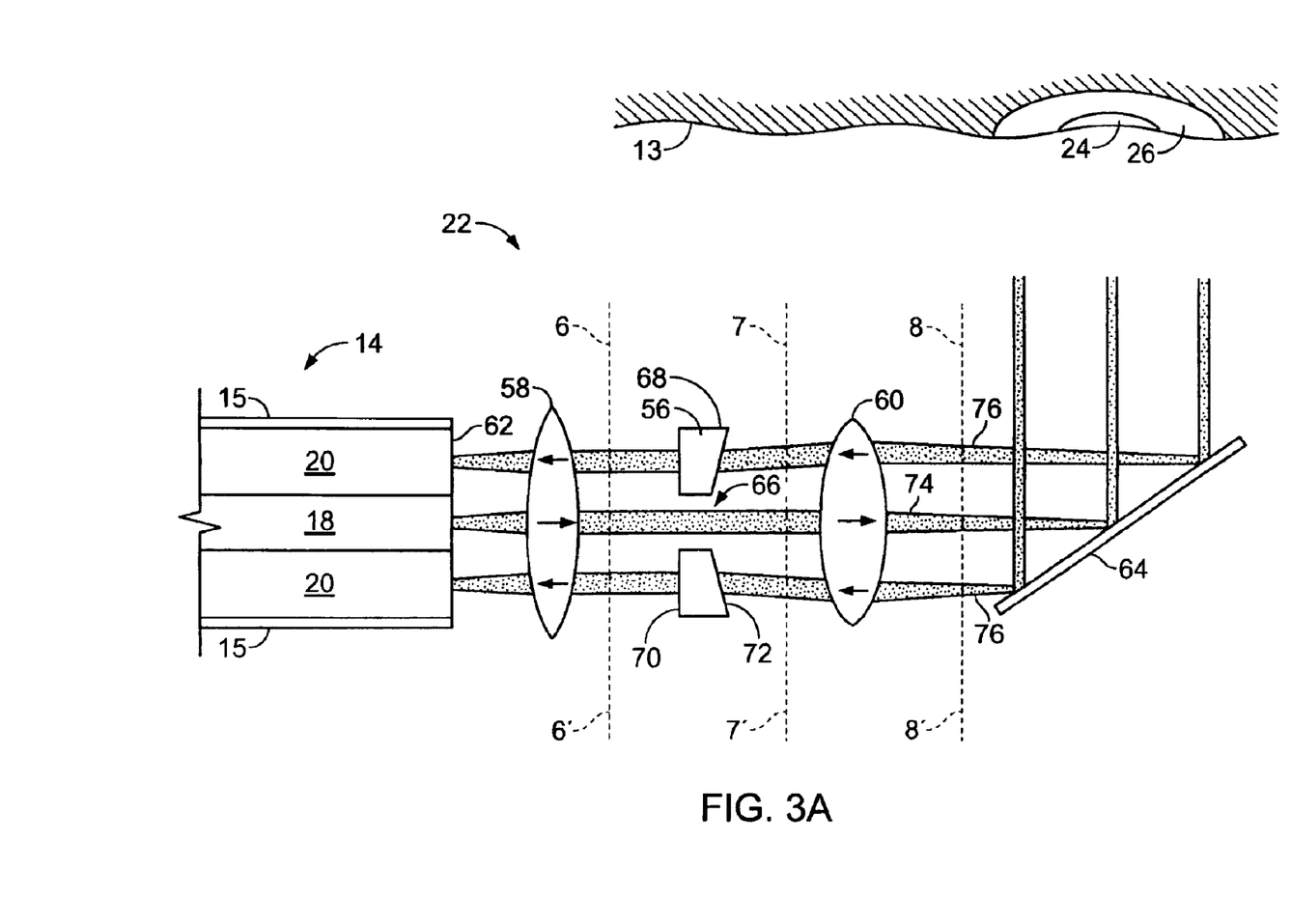
FIG. 3A is a distal tip assembly of the catheter in FIG. 1.

Referring now to FIG. 3A, at the distal end 21 of the catheter 16, a tip assembly 22 directs light traveling axially on the fiber core 18 toward an illumination spot 24 on the arterial wall 13. The tip assembly 22 also collects light from a collection area 26 on the arterial wall 13 and directs that light into the inner cladding layer 20.

As shown in FIG. 1, a rotary coupler 28 driven by a motor 30 engages the proximal end 23 of the catheter 16. When the motor 30 spins the multi-channel coupler 28, both the coupler 28 and the catheter 16 spin together as a unit. This feature enables the diagnostic system 10 to circumferentially scan the arterial wall 13 with the illumination spot 24.

In addition to spinning the catheter 16, the rotary coupler 28 guides light from a laser 32 (or other light source) into the fiber core 18 and guides light emerging from the collection portion 20 into a detector (not shown).

The detector provides an electrical signal indicative of light intensity to an amplifier 36 connected to an analog-to-digital ("A/D") converter 38. The A/D converter 38 converts this signal into data that can be analyzed by a processor 40 to identify the presence of a vulnerable plaque 12 hidden beneath the arterial wall 13.

Distal Tip Assembly

Figure 4:
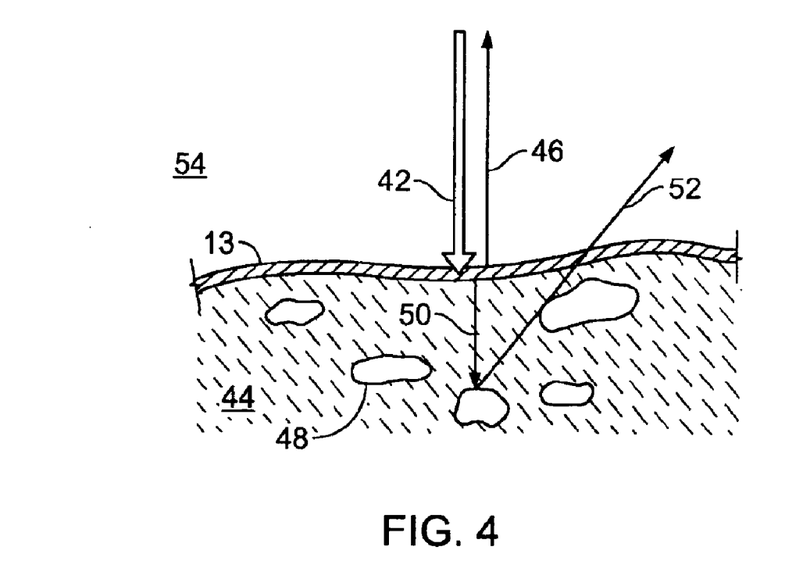
FIG. 4 is an illustration of how a collection beam is formed by light incident on an arterial wall.

When light illuminates an arterial wall 13, as shown in FIG. 4, a portion of the incident light 42 is reflected from the wall 13. This specular reflection 46 carries little or no information about structures 48 behind the arterial wall 13 and is therefore of little value. The remaining portion 50 of the incident light 42 penetrates the arterial wall 13. Some of this penetrating light 50 is absorbed. A remaining portion 52 is scattered by structures 48 behind the wall 13. After having been scattered, an even smaller portion of this remaining portion 52 again passes through the arterial wall 13 and re-enters the lumen 54. This remnant of the light originally incident on the wall, which is referred to herein as the "re-entrant light 52," carries considerable information about the structures 48 behind the arterial wall 13. It is therefore this re-entrant light 52 that the distal tip assembly 22 is intended to recover.

A first step in recovering this limited amount of re-entrant light 52 is to identify those portions of the arterial wall 13 from which this light 52 is expected to re-enter the lumen. As suggested by FIG. 4, re-entrant light 52 tends to re-enter the lumen along an annulus that is radially separated from the specularly reflected light 46. The extent of this radial separation corresponds roughly to the extent to which photons of re-entrant light 52 penetrated past the arterial wall 13 before being scattered. Consequently, the arterial wall 13 can be thought of as being divided into concentric rings of light. The particular light ring through which a photon of re-entrant light 52 re-enters the lumen 54 corresponds roughly to the depth to which that photon penetrated behind the arterial wall 13.

One approach to capturing the re-entrant light 52 is to configure the distal tip assembly 22 to capture light from a section of one of these light rings. A disadvantage of this approach is that at best, it captures no more than a small fraction of the available re-entrant light 52. A far better approach is to configure the distal tip assembly 22 so that its field of view matches, as closely as possible, the ring through which re-entrant light 52 re-enters the lumen 54.

The distal tip assembly 22, shown in more detail in FIG. 3A, separates specularly reflected light 46 from re-entrant light 52 by preferentially collecting light originating from one of these light rings. Within the distal tip assembly 22, an annular wedge prism 56 is disposed between proximal and distal lenses 58, 60. A distal face 62 of the double-clad fiber 14 is held in optical communication with the proximal lens 58. A beam-redirector 64, such as a mirror or a prism, is held in optical communication with the distal lens 60.

The annular wedge prism 56 has a core zone 66 having a radius corresponding to that of the fiber core 18 and an annular wedge zone 68 having inner and outer radii corresponding to that of the inner cladding layer 20.

The core zone 66 allows light emerging from the fiber core 18 to pass unimpeded through the annular wedge prism 56. Accordingly, the core zone 66 is either a hole or an optically transmissive material having planar proximal and distal surfaces, both of which are parallel to the distal face 62 of the double-clad fiber 14.

The annular wedge zone 68 captures light emerging from a selected light ring on the arterial wall 13 and excludes light emerging from other light rings on the wall 13. The annular wedge zone 68 then directs that captured light into the inner cladding layer 20. The inner and outer radii of the light ring on the arterial wall 13 are controlled by the wedge zone's field of view. In the illustrated embodiment, the wedge zone 68 presents a planar proximal face 70 that is parallel to the distal face of the inner cladding layer 20 and a frusto-conical distal face 72 that is inclined relative to the distal face 62 of the double-clad fiber 14.

Figure 3B:
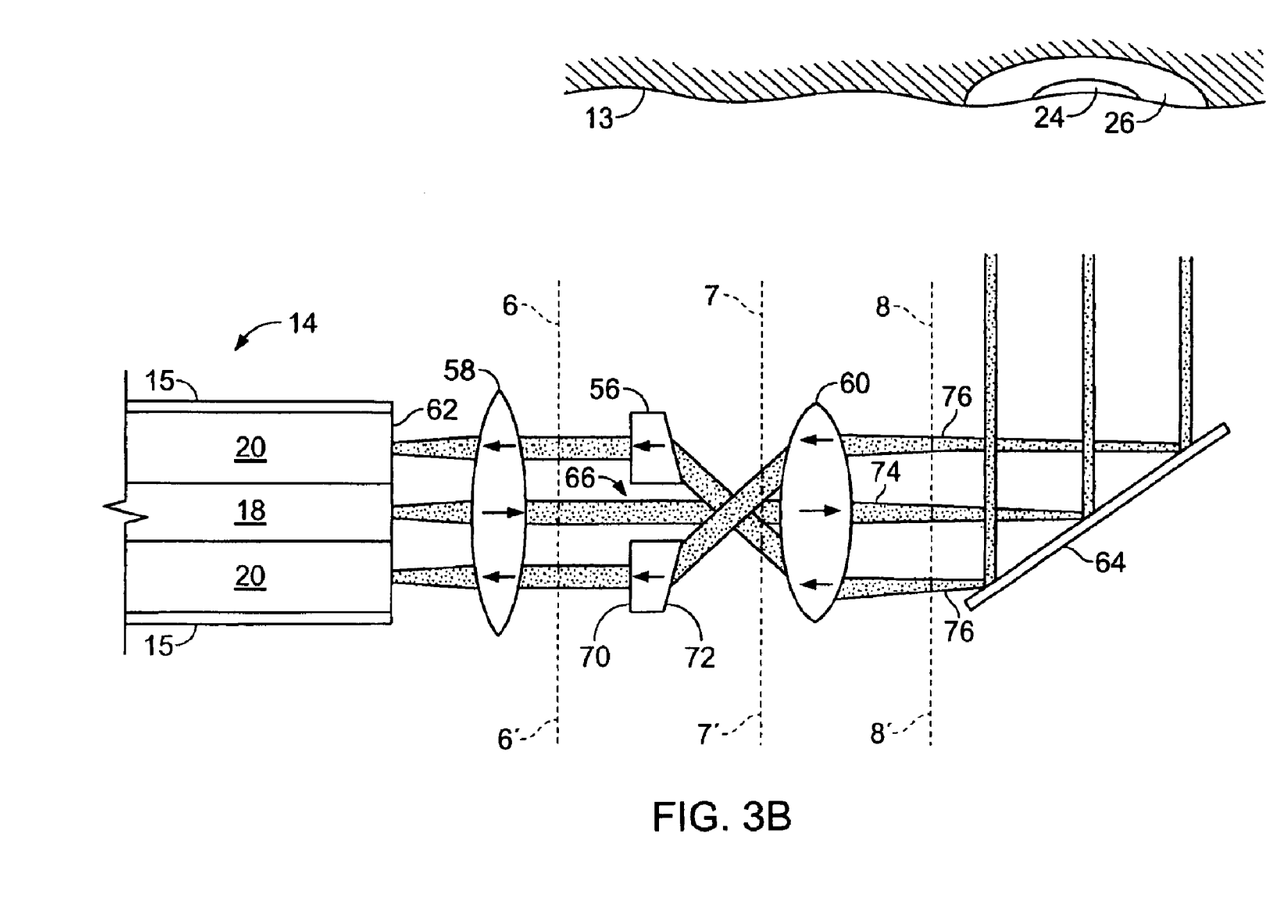
FIG. 3B is an alternate distal tip assembly of the catheter in FIG. 1.

In FIG. 3B, the slope of the incline is selected such that the wedge zone 68 is thickest at its boundary with the core zone 66 and thinnest at its periphery. This corresponds to the case in which the distance between the annular wedge prism 56 and the distal lens 60 is less than the focal length of the distal lens 60. In an alternative configuration, shown in FIG. 3A, the slope of the incline is selected such that the wedge zone 68 is thickest at the periphery and thinnest at its boundary with the core zone 66. This corresponds to the case in which the distance between the annular wedge prism 56 and the distal lens 60 is greater than the focal length of the distal lens 60.

As shown in FIG. 3A, a delivery beam 74 propagating through the fiber core 18 of the double-clad fiber 14 passes through the proximal lens 58 and through the core zone 66 of the wedge prism 56. This delivery beam 74 falls on the distal lens 60, which brings it to a focus. The beam redirector 64 intercepts the delivery beam 74 and directs it radially outward to the arterial wall 13.

Meanwhile, scattered light present in the lumen of the blood vessel falls on the beam redirector 64. A portion of this scattered light, which corresponds to light emanating from a light-emitting ring on the arterial wall 13, forms an annular collection beam 76. The distal lens 60 directs this collection beam 76 toward the wedge zone 68 of the wedge prism 56. The wedge zone 68 then collimates this light and relays it to the proximal lens 58, which then focuses it into the inner cladding layer 20 of the double-clad fiber 14. As a result, light collected by the distal tip assembly 22 is predominantly that light originating from a particular light ring on the wall 13.

Figure 5:
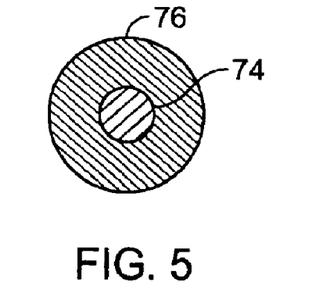
FIGS. 5–7 are cross sections of the delivery and collection beams at different planes in the distal tip assembly of FIG. 5.
Figure 6:
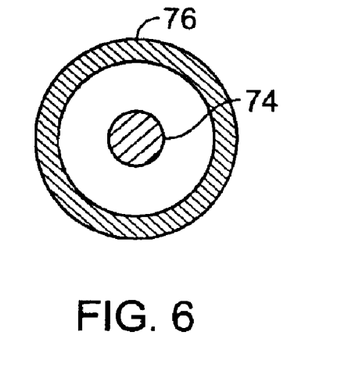
Figure 7:
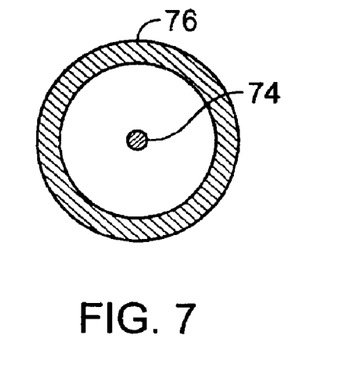

The slope of the wedge zone's inclined distal surface 72 controls the separation between the wedge zone's field of view and the core zone's field of illumination. FIGS. 5–7 show the cross sections of the annular collection beam 76 and the delivery beam 74. Proximal to the wedge prism 56, as shown in FIG. 5, the delivery beam 74 and the collection beam 76 almost overlap. Between the wedge prism 56 and the distal lens 60, as shown in FIG. 6, the delivery beam 74 and the collection beam 76 are radially separated. In FIG. 7, the delivery beam 74 and the collection beam 76 are narrower as a result of focusing by the distal lens 60.

Figure 8A:
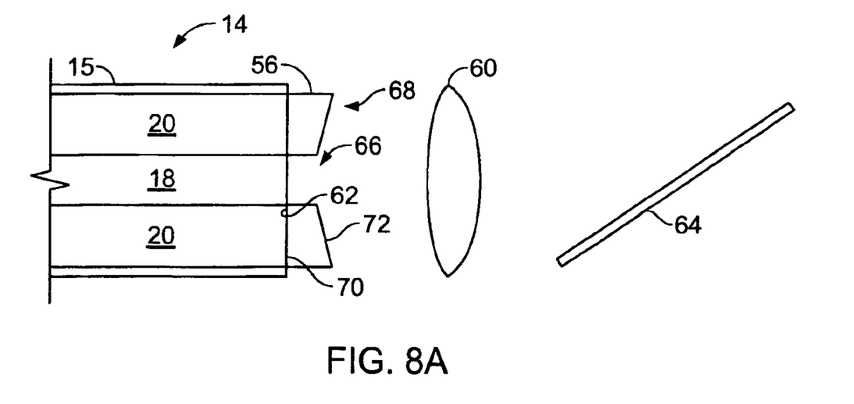
FIGS. 8A and 8B are distal tip assemblies in which the annular wedge prism contacts the double-clad fiber.
Figure 8B:
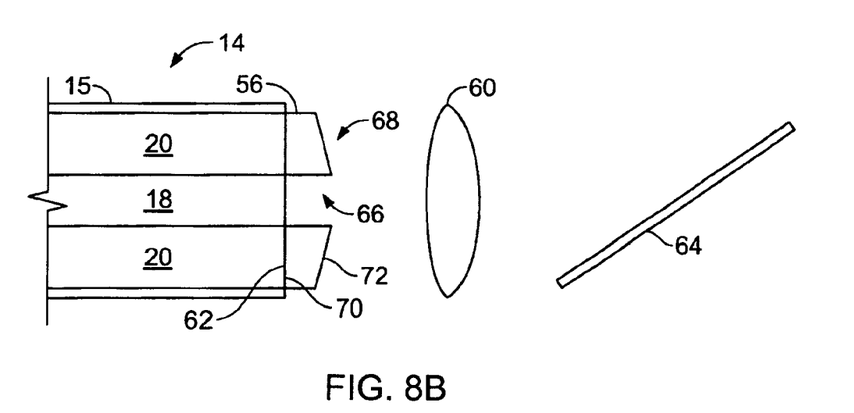
Figure 9A:
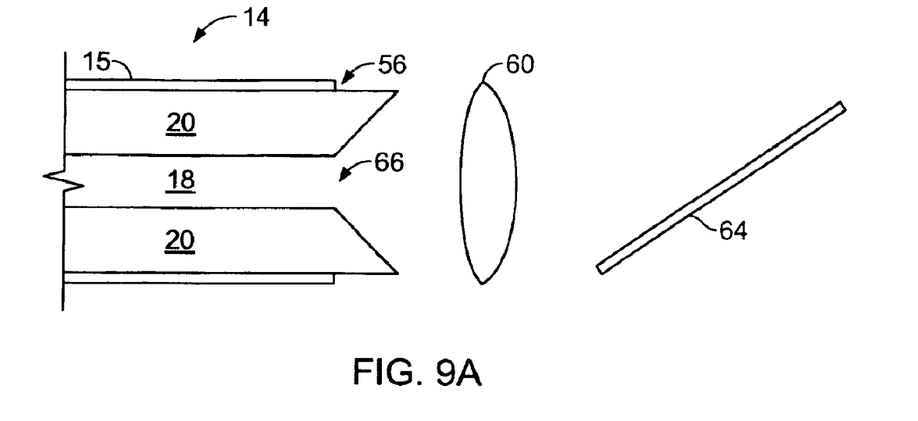
FIGS. 9A and 9B are distal tip assemblies in which the annular wedge prism is integral with the double-clad fiber.
Figure 9B:
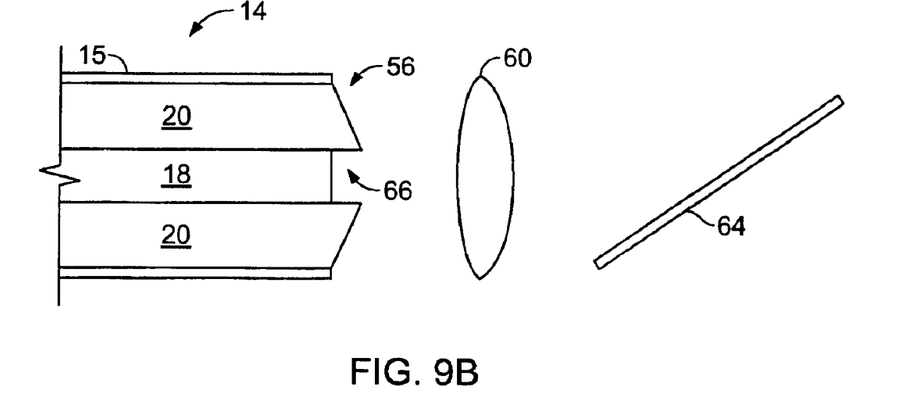

The annular wedge prism 56 need not be separated from the distal face of the double-clad fiber 14. For example, as shown in FIGS. 8A and 8B, the annular wedge prism 56 can contact the distal face 62, thereby eliminating the need for the proximal lens 58. Alternatively, the distal face 62 of the double-clad fiber 14 can be etched, as shown in FIGS. 9A and 9B, to form a wedge prism 56 that is integral with the double-clad fiber 14. The choice between the annular wedge prism 56 of FIGS. 8A and 9A and that of FIGS. 8B and 9B depends on the relative indices of refraction of the annular wedge prism 56 and the surrounding medium. If the index of refraction for the annular wedge prism 56 is greater than that of the surrounding medium, then the annular wedge prism 56 is shaped as shown in FIGS. 8A and 9A. If the index of refraction of the annular wedge prism 56 is less than that of the surrounding medium, then the annular wedge prism 56 is shaped as shown in FIGS. 8B and 9B.

Figure 10:
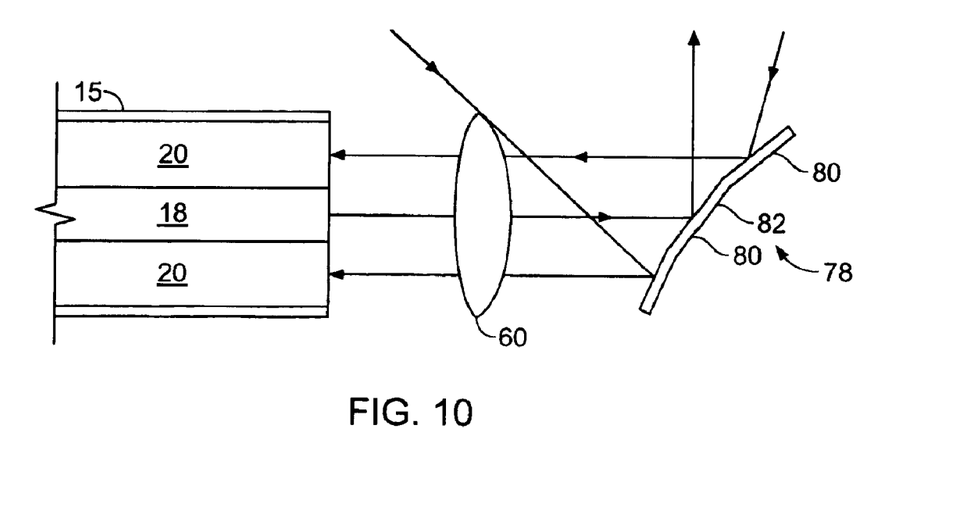
FIG. 10 is a distal tip assembly in which the beam re-director has a spatially varying slope.

The beam-directing function of the annular wedge prism 56 can also be carried out by other optical elements. For example, a beam re-director 78, as shown in FIG. 10, has an annular zone 80 and a central zone 82 having different slopes. The beam re-director 78 in this case performs the functions of both the annular wedge prism 56 and the beam re-director 64 shown in FIG. 5.

Figure 11:
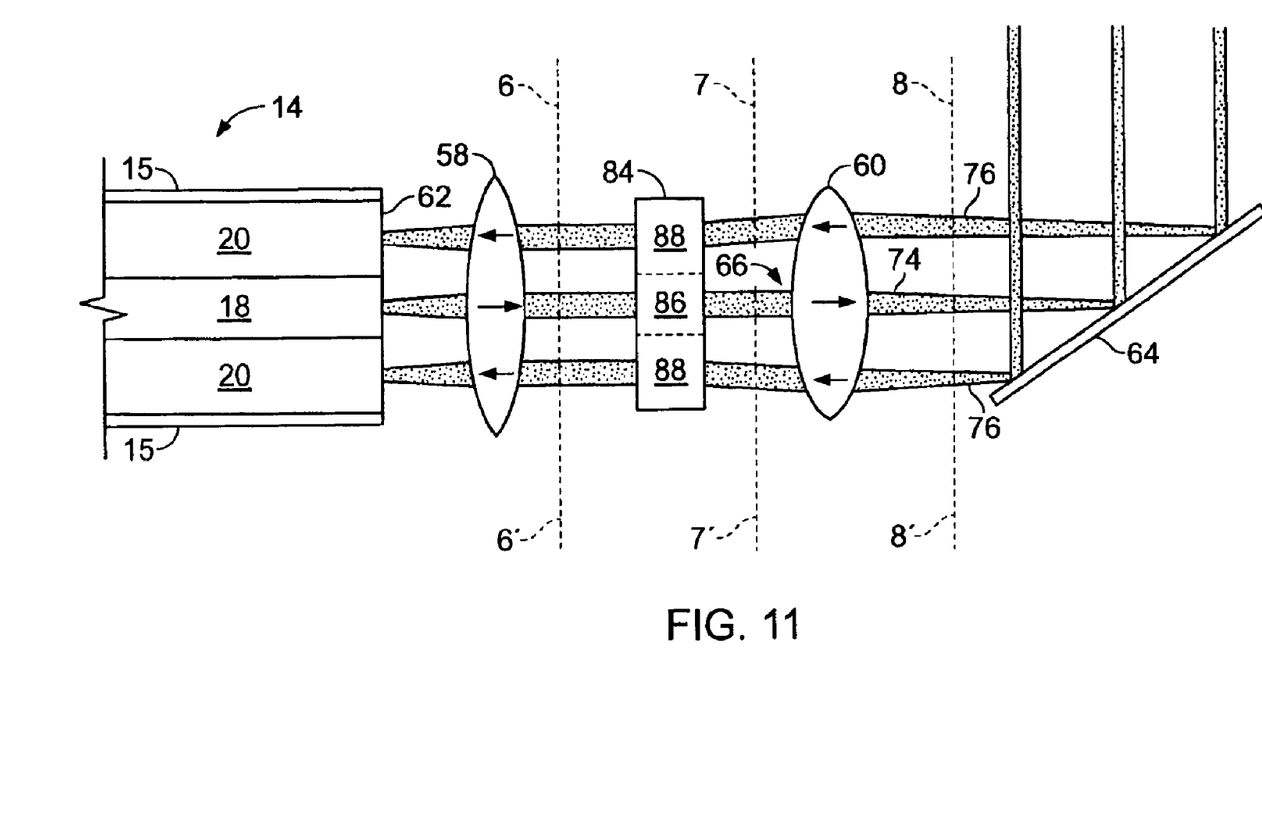
FIG. 11 is a distal tip assembly having a GRIN lens.

Another example of an optical element carrying out the function of the annular wedge prism 56 is a GRIN ("GRaduated Index of Refraction") lens 84 as shown in FIG. 11. The illustrated GRIN lens 84 includes a central sub-aperture 86 that is index-matched to the core 18 and an annular sub-aperture 88 that has a radially varying index of refraction. The optical properties of the annular sub-aperture 88 are selected to direct a collection beam into the inner-cladding layer 20.

A double-clad fiber 14 as described herein is but one example of a multi-channel fiber. Other fibers that provide multiple pathways for carrying corresponding multiple light beams can also be used. In such cases, a lens assembly is configured to have spatially separated zones that correspond to the spatially separated pathways on the multi-channel fiber. For example, an optical fiber that has several annular layers of cladding, each of which can carry a beam, can be used to collect light from a number of light rings simultaneously.

In addition, the invention is not limited by the direction in which light travels on the different channels of a multi-channel optical fiber. For example, the distal tip assembly 22 can be used to illuminate a ring on the wall and to collect light from a spot at the center of that ring. For multi-channel optical fibers having more than two channels, a particular channel can be used for illumination or collection independently of other channels.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A catheter comprising:
   a double-clad fiber extending along an axis of the catheter, the double-clad fiber having a core a first annular cladding surrounding the core; and a second annular cladding integral with the first annular cladding; and
   a lens assembly having a first sub-aperture in optical communication with the core and a second sub-aperture in optical communication with the first annular cladding.

2. The catheter of claim 1, further comprising a beam re-director in optical communication with the lens assembly.

3. The catheter of claim 2, wherein the beam re-director is selected from the group consisting of a mirror and a prism.

4. The catheter of claim 1, wherein the lens assembly comprises an annular wedge prism.

5. The catheter of claim 4, wherein the annular wedge prism comprises walls forming a hole that defines the first sub-aperture.

6. The catheter of claim 4, wherein the annular wedge prism comprises a central zone having planar proximal and distal faces, the central zone defining the first sub-aperture.

7. The catheter of claim 4, wherein the annular wedge prism comprises an annular zone having a frusto-conical face.

8. The catheter of claim 1, wherein the lens assembly is configured to cause a first beam entering the first sub-aperture and a second beam entering the second sub-aperture to diverge from each other.

9. The catheter of claim 1, wherein the lens assembly comprises a GRIN ("graduated index of refraction") lens.

10. The catheter of claim 9, wherein the GRIN ("graduated index of refraction") lens comprises a central sub-aperture that is index-matched to the core of the double-clad fiber.

11. The catheter of claim 10, wherein the GRIN ("graduated index of refraction") lens further comprises an annular sub-aperture having a radially varying index of refraction.

12. The catheter of claim 9, wherein the GRIN ("graduated index of refraction") lens is an annular lens.

13. The catheter of claim 4, wherein the annular wedge prism comprises a proximal face that is in contact with a distal face of the double-clad fiber.

14. The catheter of claim 1, wherein the lens assembly is in contact with the double-clad fiber.

15. The catheter of claim 1, wherein the lens assembly is integral with the double-clad fiber.

16. The catheter of claim 15, wherein a distal face of the double-clad fiber is shaped to form a portion of the lens assembly.

17. The catheter of claim 16, wherein the distal face of the double-clad fiber comprises sloped walls forming a recess.

18. The catheter of claim 1, wherein the lens assembly comprises a beam-redirector, the beam-redirector having a central sub-aperture oriented to re-direct a beam in a first direction and an annular sub-aperture oriented to re-direct a beam in a second direction different from the first direction.

19. A distal tip assembly for a catheter, the distal tip assembly comprising:
   a lens assembly for optically coupling to a multi-channel fiber having at least
      a first channel for transmitting light carrying a first signal,
      a second channel for transmitting light carrying a second signal, the second channel confining light carrying the first signal in the first channel, and
      a cladding layer to confine light carrying the second signal in the second channel,
   the lens assembly having
      a first sub-aperture for optically coupling to the first channel of the multi-channel fiber, and
      a second sub-aperture surrounding the first sub-aperture for optically coupling to the second channel of the multi-channel fiber.

20. The distal tip assembly of claim 19, wherein the lens assembly comprises a prism having a first sub-aperture and a second sub-aperture, the first and second sub-aperture being in optical communication with first and second channels of the multi-channel fiber.

21. The distal tip assembly of claim 19, wherein the first and second sub-apertures are disposed to optically couple a double-clad fiber having a core and an annular cladding layer surrounding the core.

22. The distal tip assembly of claim 20, wherein the prism comprises an annular wedge prism.

23. The distal tip assembly of claim 21, wherein the lens assembly comprises an annular wedge prism having a central sub-aperture disposed for optical coupling with the core of the double-clad fiber and an annular sub-aperture disposed for optical coupling with the annular cladding layer of the double-clad fiber.

24. A method for coupling light into and out of an optical catheter, the method comprising:
   providing a multi-channel optical fiber extending along the catheter, the multi-channel optical fiber having at least
      a first channel for transmitting light carrying a first signal, and
      a second channel for transmitting light carrying a second signal, the second channel confining light carrying the first signal in the first channel;
   directing a delivery beam from the first channel in a direction away from the optical catheter; and
   directing light incident on the optical catheter into the second channel.

25. The method of claim 24, wherein providing a multi-channel optical fiber comprises providing a double-clad fiber having a core and an annular cladding layer.

26. The method of claim 24, wherein directing a delivery beam from the first channel in a direction away from the optical catheter comprises:
   providing a lens element having first and second sub-apertures; and
   optically coupling the first sub-aperture to the first channel.

27. The method of claim 24, wherein directing light incident on the optical catheter into the second channel comprises:
   providing a lens element having first and second sub-apertures; and optically coupling the second sub-aperture to the second channel.

* * * * *